United States Patent
Aitani et al.

(10) Patent No.: US 10,844,294 B2
(45) Date of Patent: Nov. 24, 2020

(54) CATALYTIC CRACKING OF CRUDE OIL TO LIGHT OLEFINS

(71) Applicant: KING FAHD UNIVERSITY OF PETROLEUM AND MINERALS, Dhahran (SA)

(72) Inventors: Abdullah Mohammed Aitani, Dhahran (SA); Sulaiman Saleh Al-Khattaf, Dhahran (SA); Akram Abdulhakeem Al-Absi, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/353,465

(22) Filed: Mar. 14, 2019

(65) Prior Publication Data

US 2020/0291306 A1    Sep. 17, 2020

(51) Int. Cl.
*C10G 51/02* (2006.01)
*B01J 29/80* (2006.01)
(Continued)

(52) U.S. Cl.
CPC .......... *C10G 51/026* (2013.01); *B01J 8/1827* (2013.01); *B01J 8/26* (2013.01); *B01J 29/40* (2013.01); *B01J 29/70* (2013.01); *B01J 29/80* (2013.01); *B01J 35/109* (2013.01); *B01J 35/1019* (2013.01); *B01J 35/1038* (2013.01); *C07C 4/06* (2013.01); *C07C 2521/04* (2013.01); *C07C 2521/08* (2013.01); *C07C 2521/12* (2013.01);
(Continued)

(58) Field of Classification Search
CPC ................ C10G 51/026; B01J 29/80

USPC .... 585/648, 651, 653; 208/120.01, 119, 118
See application file for complete search history.

(56) References Cited

U.S. PATENT DOCUMENTS 2,464,810 A * 3/1949 Hirsch ................... C10G 11/18
                                                    208/113
6,791,002 B1   9/2004 Abrevaya et al.
(Continued)

FOREIGN PATENT DOCUMENTS

CN         102746889 B      5/2015
WO     WO 2018/220643 A1 *  1/2018  ............. B01D 45/12

OTHER PUBLICATIONS

Kun Hao, et al., "Influence of combined alkaline treatment and Fe—Ti-loading modification on ZSM-5 zeolite and its catalytic performance in light olefin production", Journal of Industrial and Engineering Chemistry, vol. 18, Issue 5, Sep. 25, 2012, pp. 1736-1740 (Abstract only).

*Primary Examiner* — Thuan D Dang
(74) *Attorney, Agent, or Firm* — Oblon, McClelland, Maier & Neustadt, L.L.P.

(57) ABSTRACT

An integrated process catalytically cracks whole light crude oil into light olefins, especially propylene and ethylene. The process is integrated with an adjacent conventional fluid catalytic cracking unit whereby the heavy liquid product mixture (light and heavy cycle oils) from whole crude oil cracking is mixed with vacuum gas oil (VGO) for further processing. The process comprises recycling total product fraction of light cracked naphtha (LCN) and mixing with fresh crude oil feed. High propylene and ethylene yields are obtained by cracking the whole light crude oil and LCN in an FCC configuration using a mixture of FCC catalyst and ZSM-5 additive at a temperature between, that of conventional FCC and steam cracking.

20 Claims, 2 Drawing Sheets

(51) Int. Cl.
  *B01J 29/40* (2006.01)
  *B01J 29/70* (2006.01)
  *B01J 35/10* (2006.01)
  *B01J 8/26* (2006.01)
  *B01J 8/18* (2006.01)
  *C07C 4/06* (2006.01)

(52) U.S. Cl.
  CPC ...... *C07C 2529/40* (2013.01); *C07C 2529/80* (2013.01); *C10G 2300/1074* (2013.01); *C10G 2300/202* (2013.01); *C10G 2300/205* (2013.01); *C10G 2300/301* (2013.01)

(56) References Cited

U.S. PATENT DOCUMENTS

| | | | |
|---|---|---|---|
| 8,394,259 B2 | 3/2013 | Palmas et al. | |
| 8,993,824 B2 | 3/2015 | Mehlberg | |
| 9,101,854 B2 | 8/2015 | Koseoglu et al. | |
| 2001/0042701 A1* | 11/2001 | Stuntz | C10G 69/04 208/68 |

* cited by examiner

CATALYTIC CRACKING OF CRUDE OIL TO LIGHT OLEFINS

BACKGROUND OF THE INVENTION

Field of the Invention

The present disclosure relates to catalytic cracking, e.g., FCC of whole crude oil and/or crude oil mixtures with lighter fractions, such as light cracked naphtha, particularly to generate C2 to C4 olefins, as well as catalysts, integrated manufacturing processes, and manufacturing systems for such cracking.

Description of the Related Art

Many refiners worldwide have begun to focus on revamping operations to co-produce petrochemicals due to an anticipated decline in demand for refined products, such as transportation fuels. During the last two decades, global demand for refined products has increased at average annual growth rate of 1.3% compared with an average increase of 3.5% for petrochemical feedstocks, driven by global population increases, improving living standards, and demographic shifts from rural to urban areas.

In 2016, the production of basic petrochemicals accounted for 12 million barrels per day (bpd) of global crude oil demand and is forecasted to increase to 18 million bpd by 2030. Ethylene and propylene are the largest-volume basic petrochemicals (light olefins) used mainly in the production of polymers and other packaging materials such as styrene, acrylonitrile, oxides of ethylene and propylene, etc. The global production capacity of ethylene and propylene is forecasted to reach 385 million tons in 2030, increasing from 240 million tons in 2016. Ethylene is mainly produced by naphtha steam cracking (SC) in addition to other feedstocks such as ethane and liquefied petroleum gas. Propylene is co-produced from fluid catalytic cracking, naphtha steam cracking, methanol to olefins, butenes metathesis, and propane dehydrogenation (PDH).

Whole crude oil conversion to chemicals (OTC) is an emerging route for the production of aromatics and light olefins that bypasses costly refining steps. The OTC route is attractive because of lower energy consumption, reduced feedstock costs, and lower $CO_2$ emissions. The stability of petrochemical prices in comparison to crude oil prices makes it advantageous to convert crude oil to petrochemical feedstocks. With advances in catalytic technology, modern complex refineries can be configured to convert crude oil directly to chemical feedstocks instead of transportation fuels. Various chemical and oil companies are investigating the conversion of whole (i.e., unprocessed) crude oil to light olefins and naphtha in order to bypass costly refining. ExxonMobil commercialized the first oil to chemicals plant in 2014 using steam cracking of light crude oil to light olefins. Recently, several companies announced plans to construct OTC complexes in Saudi Arabia, Indonesia, China, and others.

Al-Khattaf and co-workers investigated the direct catalytic cracking of various types of light crude oils using techniques such as a microactivity test (MAT) unit, riser simulator, and advanced catalytic evaluation (ACE), as described in *Chem. Eng. Res. Des.* 2017, 120, 121-137, *Energy Fuels* 2017, 31, 12677-12684, *Energy Fuels* 2018, 32, 2234-2244, and *Energy Fuels* 2018, 32, 6189-6199, each of which is incorporated in its entirety herein. The Al-Khattaf results show that various types of light crude oils can be cracked over FCC catalysts blended with ZSM-5 zeolite, and the cracked liquid products can be mixed with crude oil to enhance the production of light olefins and naphtha. Various other efforts have been made to modify conventional cracking and/or its product yields.

U.S. Pat. No. 7,019,187 to Powers (Powers) discloses a method of converting whole crude oil to light olefins. Powers's crude oil is subjected to mild catalytic cracking and gaseous products are subjected to severe cracking in the radiant section of a pyrolysis furnace for the production of light olefins. Powers radiant section relies on heat transfer from burners to radiant tubes occurring largely by radiation, where the hydrocarbon vapors are heated to from ~1,450° F. (~788° C.) to 1,550° F. (~843° C.) for "severe cracking." Powers heats the liquid hydrocarbon stream between ~800° F. (~427° C.) to ~1,300° F. (~704° C.) in a "mild catalytic steam cracking." Powers's vaporous hydrocarbon product of the mild catalytic cracking facility can be passed back into the furnace to enter the furnace's radiant section, but Powers discloses no further recycles, nor any particular catalyst combination.

U.S. Pat. No. 9,228,140 to Abba et al. (Abba) describes an integrated hydroprocessing, steam pyrolysis, and catalytic cracking process to produce light olefins and aromatics from Arabian Light crude oil (i.e., API gravity around ~33° and ~2.0 wt. % sulfur). Heavy components from Abba's steam pyrolysis are catalytically cracked and the olefins and aromatics are recovered as product streams. Abba uses a steam pyrolysis cracker, operating at 400 to 900° C., and a fluidized catalytic cracker, operated at 530 to 700° C. While Abba describes riser reactors as an option, Abba teaches that downflow reactors offer shorter residence times, e.g., 0.1 to 30, 0.1 to 10, 0.2 to 0.7 seconds, and higher catalyst-to-oil ratios, e.g., 20:1 to 30:1. In addition, Abba feeds a liquid phase from a pyrolysis to an FCC unit, but no fraction is returned to pyrolysis, let alone another FCC unit. Moreover, while Abba discloses preferred zeolites for cracking in the FCC process to be zeolites Y, REY, USY, and RE-USY, and discloses preferred catalysts for enhanced light olefin production from naphtha cracking using ZSM-5 zeolite crystal or other pentasil type catalyst structure, Abba does not mention any specific combination of zeolite catalysts, nor any ratio of such combination.

U.S. Pat. No. 9,290,705 to Bourane et al. (Bourane) uses a high-severity process for catalytically cracking crude oil to light olefins and other products, whereby crude oil is separated into a high boiling fraction and a low boiling fraction, and each fraction is processed in a separate FCC down-flow reactor. Bourane's catalyst, combined from both down-flow reactors, is regenerated in a common vessel. By combining catalyst particles from the high boiling fraction having high carbon content helps to provide additional heat for regeneration. Bourane's catalytic cracking of Arab Extra Light crude oil (i.e., API gravity of ~39 to 40° and ~1.1 wt. % sulfur) at 600° C. and catalyst-to-oil (C/O) ratio of 31 yielded 5.2 wt % ethylene and 15.8 wt % propylene. Bourane recycles catalyst and heavy cycle oil and/or slurry oil to downflow reactor processing of the light fraction, whereby the recycle stream maintains heat balance of Bourane's operation. However, Bourane describes neither recycling any fraction, e.g., light cracked naphtha, from an FCC unit to another cracker, nor using a particular combination of catalysts.

U.S. Pat. No. 6,791,002 to Abrevaya et al. (Abrevaya) discloses a riser reactor system for conversion of hydrocarbon feedstock to ethylene and propylene. Abrevaya's riser reactor system has riser reactors with a plurality of feeding gas inlet ports having different compositions and for controlling the residence time of a gas catalyst within the riser reactor. Abrevaya does not disclose mixing light cracked naphtha with fresh crude oil and subjecting the mixture to cracking in a riser reactor. Abrevaya does not disclose mixing light cracked naphtha with fresh crude oil, and cracking the mixture in a riser reactor. Abrevaya's reactor system is designed for multiple hydrocarbon feed streams, which may include a feed of naphtha, gas oil, vacuum gas oil, FT wax, or mixture thereof, without mixing a recycled aromatics-free stream into a feed. Moreover. Abrevaya does not disclose feeding oils from a cracker to an FCC unit, but instead feeding uppers, i.e., gases, from a first riser to a second riser in an embodiment, or multiple component streams from a separator to a riser.

CN 102746889 B to Wang et al. (Wang) discloses a method for producing ethylene and propylene by catalytic cracking, reporting improved ethylene and propylene yields acrd a low propylene to ethane ratio. Wang uses two fluidization reactors for catalytic cracking, wherein C4 to C12 naphtha enters a first riser of a fluidization catalytic cracking reactor at 600 to 750° C., 4 to 0.3:1 catalyst-to-naphtha weight ratio, and 1 to 40:1 water-to-naphtha weight ratio. Non-aromatic C5-C12 hydrocarbons enter a second riser of the first reactor operated within the same ranges as the first riser, and a C4 component from two risers enters a second fluidization reactor for catalytic cracking. Ethylene and propylene are obtained in up to 54% yield by separating the effluent from two fluidization reactors. However, Wang does not disclose catalytic cracking of a light crude oil to light olefins, nor mixing light cracked naphtha with fresh crude oil and subjecting the mixture to cracking in a riser reactor. Wang instead catalytically cracks naphtha in two riser reactors with no recycling between them.

U.S. Pat. No. 8,993,824 to Mehlberg (Mehlberg) discloses a process for fluid catalytic cracking, including a first feed having a boiling point of 180 to 800° C. to a first riser reactor, and a second feed having first and second parts to a second reactor. Mehlberg's typical first part includes C5-C12 hydrocarbon(s) and a second part includes C4-C5 hydrocarbon(s). An effective amount of the second part is combined with the first part to maximize production of propylene. Mehlberg's second riser (operating at 425 to 630° C.) is mainly designed to eliminate butenes at a higher temperature than the first riser (operating at 150 to 580° C.). Mehlberg's feed from the first to the second riser includes naphtha, light cracked naphtha, and polygas, and C4$^=$, e.g., butene, is added to increase the propylene yield. However, Mehlberg does not disclose mixing light cracked naphtha with fresh crude oil and subjecting the mixture to cracking in a riser reactor. Moreover, Mehlberg's isothermal riser reactor is operated at 566° C. a riser pressure of 270 kPa, a feed partial pressure of 140 kPa, and a catalyst-to-oil weight ratio of 8:1 to 12:1.

U.S. Pat. No. 9,101,854 to Koseoglu et al. (Koseoglu) discloses a system and method of cracking hydrocarbon feedstocks including introducing the feedstock and hydrogen into a first hydrocracking reaction zone containing a first hydrocracking catalyst to produce a first zone effluent, passing the first zone effluent and optionally additional hydrogen to a second hydrocracking reaction zone containing a second hydrocracking catalyst to produce a second zone effluent, conveying the second zone effluent to a fractionating zone to obtain at least a low boiling fraction and a high boiling fraction, and optionally one or more intermediate fractions, and passing the bottoms fraction to a fluidized catalytic cracking reaction and separation zone, from which olefins and gasoline are recovered. Remaining cycle oil is at least partially passed from the fluidized catalytic cracking reaction and separation zone to the first and/or second hydrocracking reaction zone. Kaseoglu's first two reactors optionally operate in hydrocracking mode, consuming $H_2$, to increase fuel production. Koseoglu may recycle cycle oil to its feedstock, or a portion of overhead gases to its hydrocrackers, but Koseoglu does not disclose mixing light cracked naphtha with fresh crude oil, nor cracking the mixture.

U.S. Pat. No. 8,394,259 to Palmas et al. (Palmas) discloses a fluid catalytic cracking unit including a first riser, a second riser, and a disengagement zone. The first riser can receive a first feed terminating at a first reaction vessel having a first volume. The second riser can receive a second feed terminating at a second reaction vessel having a second volume. Generally, the first volume is greater than the second volume. The disengagement zone can receive a first mixture including catalyst(s) and product(s) from the first reaction vessel, and a second mixture including catalyst(s) and product(s) from the second reaction vessel. Typically, the first mixture is isolated from the second mixture. However, Palmas does not disclose mixing light cracked naphtha with fresh crude oil, nor cracking the mixture in a riser reactor. Instead, Palmas aims to produce gasoline and propylene using two risers and one engagement zone.

J. Indus. Eng. Chem. 2012, 18(5), 1736-1740 by Hao et al. (Hao) discloses alkali treatment and Fe—Ti-loading to modify ZSM-5 zeolite. Hao reports that the alkali treatment creates mesopores and the Fe—Ti-loading improves the redox property of ZSM-5, while both modifications lead to a reduction of the total count of acid sites. Hao's catalytic performance test indicated that the coexistence of meso-microporosity and Fe—Ti-loading on the ZSM-5 catalyst improves the yield of light olefins in catalytic cracking. Hao's catalyst, containing the combined modified ZSM-5, increased the propylene yield by 0.55 wt. % and total light olefins yield by 0.69 wt. % in catalytic cracking of Canadian LGO (light gas oil), compared with a reference HZSM-5. Hao describes modifying zeolite catalyst properties, e.g., mesoporosity, and reducing acidity by metal impregnation to slightly increase light olefins by cracking light gas oil. However. Hao does not disclose mixing light cracked naphtha with fresh crude oil, nor cracking the mixture.

In light of the above, a need remains for improved cracking methods and layouts, particularly for producing light olefins, such as ethylene and propylene, and modifying the composition ratios of these, as well as catalyst combinations affecting such outcomes. Accordingly it is one object of the present disclosure to provide an integrated system and process, and related catalysts, for catalytic cracking of whole or substantially unfractionated crude oil with an adjacent conventional FCC unit to co-process a mixture of vacuum gas oil (VGO) and cycle oils produced from whole crude oil cracking. It is another object to provide an integrated process that comprises catalytic cracking of a mixture of whole crude oil feed and recycled light cracked naphtha (LCN) for the production of light olefins, especially propylene and ethylene.

SUMMARY OF THE INVENTION

Aspects of the invention provide methods comprising: feeding a crude oil to a riser reactor comprising a fluidized catalyst for cracking at a temperature in a range of from 525 to 800° C., the crude oil being at least 75 wt. % unfractionated, preferably at least 80 wt. %, at least 85 wt. %, at least 90 wt % or at least 95 wt. % unfractionated, to obtain a mixture of cracked products; separating the cracked products into fractions comprising light olefins, light cracked naphtha (LCN) having a boiling range of front 20 to below 121° C., preferably from 40 to below 115° C., 50 to below 110° C., or 60 to below 100° C., heavy cracked naphtha (HCN) having a boiling range of from 121 to 221° C., preferably 125 to 215° C., 130 to 210° C. or 1140 to 200° C. and optionally combined light and heavy cycle oil (LCO, HCO) fractions, respectively having a boiling range of from 221 to 343° C., and above 343° C., respectively; co-feeding a mixture comprising at least portions of the LCO and the HCO to a fluid catalytic cracker (FCC) unit comprising an FCC catalyst; cycling at least a portion of the LCN from the riser reactor and/or LCN from the FCC unit back to the feeding with the crude oil; and optionally, repeating. Any of the features described herein may augment or supplement the above in any permutation, particularly those described as inventive to follow.

The light olefins may comprise at least 25 wt. % ethylene and propylene, preferably 25 to 55 wt. %, 30 to 50 wt. % or 35 to 45 wt. % based on a total light olefin weight. The riser reactor may be operated at a pressure in a range of from 0.5 to 2.0 bar, preferably from greater than 1.0 to 1.5 bar, and/or at a temperature a range of from 600 to 700° C., preferably 620 to 650° C.

The FCC catalyst may comprise: ZSM-5 in an amount in a range of from 10 to 45 wt. %, preferably 15 to 40 tint %, 20 to 35 wt. % or 25 to 30 wt. % of the total catalyst weight; and a different zeolite in an amount of at least 50 wt. % of the total catalyst weight. The ZSM-5 may have a $SiO_2$-to-$Al_2O_3$ molar ratio in a range of from 4.5 to 6.5, preferably 5.0 to 6.0 or about 5.5, a BET surface area in a range of from 115 to 135 $m^2/g$, a micropore volume in a range of from 0.04 to 0.06 $cm^3/g$, a mesopore volume in a range of from 0.03 to 0.05 $cm^3/g$, and/or a total acidity of 0.3 to 0.6 mmol/g, preferably 0.4 to 0.5 mmol/g. The different zeolite may have a $SiO_2$-to-$Al_2O_3$ molar ratio in a range of from 2.5 to 4.5, preferably 3.0 to 4.0 or about 3.5, a BET surface area in a range of from 145 to 175 $m^2/g$, a micropore e in a range of from 0.05 to 0.07 $cm^3/g$, mesopore volume in a range of from 0.06 to 0.18 $cm^3/g$, and/or a total acidity of 0.03 to 0.15 mmol/g, preferably 0.05 to 0.1 mmol/g.

The crude oil may be unfractionated, may have an API gravity of at least 30°, may comprise no more than 5 wt. % sulfur, 20 ppm V, and/or 5 ppm Ni. A feed for the FCC unit may comprise the mixture, i.e., comprising LCO and HCO, and vacuum gas oil (VGO) having a boiling range of from 250 to 585° C. The VGO may be from the first cracker unite and/or from another source.

The FCC unit may be directly downstream of the riser reactor. Directly downstream meats that the stream exiting the riser reactor is not subject to any compositional or physical changes after exiting the riser reactor and entering the FCC unit. Inventive methods may comprise separating products from the FCC unit into fractions comprising light olefins, light cracked naphtha (LCN) having a boiling range of from 20 to below 121° C., heavy cracked naphtha (HCN) having a boiling, range of from 121 to 221° C., light cycle oil (LCO) having a boiling range of from 221 to 343° C., and heavy cycle oil (HCO) having boiling points above 343° C.

The feeding may use a feed comprising the crude oil and 2 to 20 wt. % of the LCN based on a total feed weight. The fluidized catalyst may be different from the FCC catalyst. A catalyst-to-oil weight ratio in the riser reactor and/or the FCC unit may be in a range of from 25 to 50.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
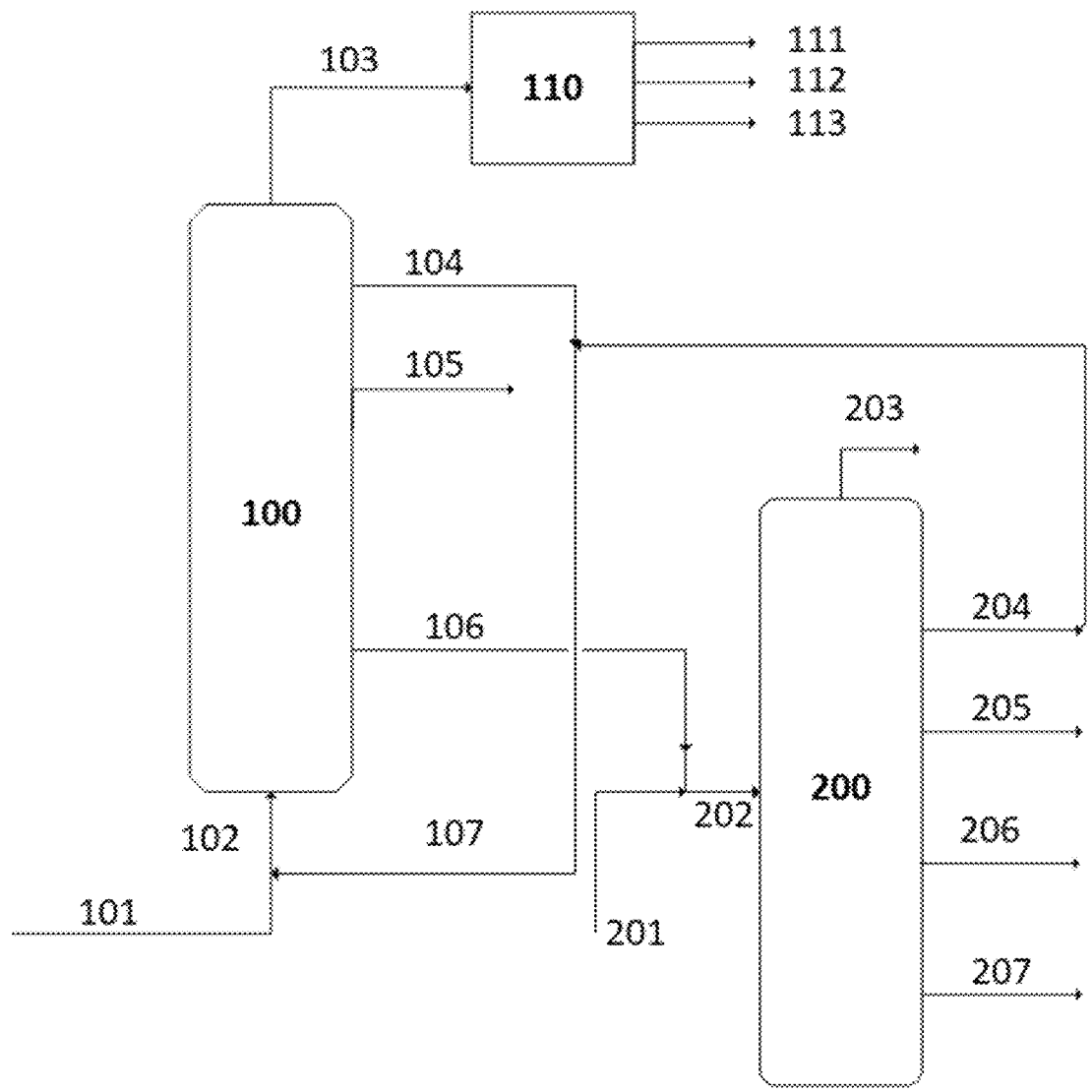
FIG. 1 shows a flow diagram of integrated process for whole crude oil catalytic cracking to light olefins and integration with a conventional FCC unit.

As used herein, the term "whole crude oil" as used herein means crude oil as it issues from a wellhead except for any treatment such crude oil may receive to render it acceptable for conventional distillation in a refinery, such as dewatering, desalting, and/or sweetening, not having undergone any distillation or fractionation. "Whole crude oil" is crude oil suitable for distillation or other fractionation in a refinery, and may comprise non-boiling entities such as asphaltenes or tar. Such "whole crude oil" may be crude oil(s) straight from an oil field pipeline and/or conventional crude oil storage facility, without any prior fractionation thereof.

While whole crude oil is exemplified, distilled and/or fractionated components or component mixtures may be used, such as those comprising gaseous fuel, pet ether/gasoline, naphtha, kerosene and jet fuel, diesel and fuel oil, atmospheric oil, motor oil, light and heavy vacuum oil, ship fuel, grease, wax, tar/bitumen, or mixtures of 2, 3, 4, 5 or more of any of these, including a high boiling residues.

The term "catalytic cracker" as used herein may identify fluidized or non-fluidized arrangements, unless identified otherwise. The crackers may be in side-by-side or stacked configuration, or both, with 1, 2, 3, 4, 5, or more reactors or reactor zones of either or both configurations arranged in series and/or parallel. Unless otherwise specifically limited, the cracker(s) and/or cracker set-up(s) may be further arranged for isomerization, dehydrogenenation, hydrogen transfer, cyclization, condensation, alkylation, and/or dealkylation. Although typical feedstocks for cracking may be vacuum and atmosphere gas oil at least one of the crackers herein uses heavier stream(s), especially crude oil, especially whole crude oil. The heavier stream feedstocks are generally subjected to preheating before entering the cracker(s).

Aspects of the invention provide methods comprising, generally after preheating the feed, feeding a crude oil to a catalytic cracker, e.g., a riser reactor comprising a fluidized cracking catalyst, at a temperature in a range of from 525 to 800° C. The crude oil may be at least 75, 80, 85, 90, 91, 92, 92.5, 93, 94, 95, 96, 97, 97.5, 98, 99, 99.1, 99.5, or 99.9 wt. % unfractionated. The crude oil may preferably be Light Arabian crude, or anything lighter than that, including blends, but may even be (optionally lightened) Boscan, Tia Juana Heavy, or even tar sand, and may particularly be detarred and/or deasphalted fractions of otherwise heavy oils. Likewise, the crude oil may be a sweetened crude, such as initially sour Venezuelan varieties. The obtained cracked products may be separated into fractions. The fractions will generally include liquid and gas components, i.e., at standard temperature and pressure. The fractions may comprising dry gas(es) optionally including light olefins and/or liquefied petroleum gas (LPG), light cracked naphtha (LCN) having a boiling range of from 20 to below 121° C., heavy cracked naphtha (HCN) having a boiling range of from 121 to 221° C., light cycle oil (LCO) having a boiling range of from 221 to 343° C., and heavy cycle oil (HCO) having boiling points above 343° C., whereby any of the LPG, LCN, HCN, LCO, and/or HCO may be unified into a single fraction. Heavier crudes or crude compositions may have further fractions including tars, asphaltenes, and non-boilers, which would make out either further fractions or be separated prior to feeding. A mixture comprising at least portions of the LCO and the HCO from a first cracker, preferably at least 75, 85, 90, 92.5, 95, or 97.5 wt. % of the total weight of LCO and/or HCO from the first cracker, may be co-fed to a (generally adjacent and/or without intervening reaction, catalyst regeneration, and/or separation zone(s)) fluid catalytic cracker (FCC) unit comprising an FCC catalyst. The FCC unit and/or the first cracker may cycle at least a portion of the LCN produced, i.e., at least 75, 80, 85, 90, 91, 92, 92.5, 93, 94, 95, 96, 97, 97.5, 98, 99, 99.1, 99.5, or 99.9 wt. % of a total LCN weight of either or both, back to the feeding with the crude oil. The return(s) of the LCN may rejoin the crude feed and/or separately enter the first cracker, with optional intervening purification and/or fractionation steps. Generally, inventive processes will, be continuous, such that the aforementioned steps are repeated.

The light olefins separated off of the first cracker and/or the FCC unit may comprise at least 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, or 85 wt. % ethylene and propylene, based on a total light olefin weight. The weight ratio of propylene to ethylene may be, for example, above 1.80, 1.81, 1.82, 1.83, 1.84, 1.85, 1.86, 1.87, 1.88, 1.89, 1.90, 1.91, 1.92, 1.93, 1.94, or 1.95.

The first cracker, e.g., riser reactor, may be operated at a pressure in a range of from 0.5 to 2.0, 0.75 to 1.75, 1 to 1.5, or 1.2 to 1.4 bar-a, and/or at least 0.6, 0.7, 0.8, 0.9, 1.05, 1.1, 1.25, or 1.33 bar-a, and/or no more than 2.5, 2.25, 1.9, 1.8, 1.7, 1.6, 1.5, 1.33, or 1.2 bar-a. Additionally or separately, the first cracker, e.g., riser reactor, may be operated at a temperature in a range of from 600 to 700, 625 to 675, or 640 to 660° C., and/or at least 615, 620, 630, 635, 645, or 650° C., and/or no more than 725, 715, 695, 685, 667, 655, or 650° C. The LCN cycled back to, the cracker may be at least 25, 33, 50, 65, 75, 80, 85, 90, 91, 92, 92.5, 93, 94, 95, 96, 97, 97.5, 98, 99, 99.1, 99.5, or 99.9 wt. % of a total weight of the LCN produced by the first cracker and/or the FCC unit.

The FCC catalyst may comprise ZSM-5 and a different zeolite and/or equilibrium catalyst. The ZSM-5 may be in an amount in a range of from 10 to 40, 15 to 37.5, 15 to 35, 20 to 35, 25 to 35, or 22.5 to 30 wt. % of the total FCC catalyst weight, and/or at least 12.5, 14, 16, 17.5, 19, 21, 23, 26, 27.5, or 30 wt. %, anti/or no more than 50, 45, 40, 37.5, 35, 32.5, 30, or 27.5 wt. %. The different zeolite, i.e., E-Cat, may be in an amount of at least 50, 60, 70, 75, 80, 85, 90, or 95% wt. % of the total FCC catalyst weight, e.g., 60 to 80, 65 to 75, or 67.5 to 72.5 wt. %. The ZSM-5 and different zeolite may make out all of the FCC catalyst weight, i.e., no other catalytic component or even no further carrier, or at least 75, 80, 85, 90, 91, 92, 92.5, 93, 94, 95, 96, 97, 97.5, 98, 99, 99.1, 99.5, or 99.9 wt. % of a total FCC catalyst weight. The ZSM-5 may have a $SiO_2$-to-$Al_2O_3$ ratio in a range of from 4.5 to 6.5, 4.75 to 6.25, 5.0 to 6.0, 5.1 to 5.9, 5.2 to 5.8, 5.3 to 5.75, 5.4 to 5.7, or 5.5 to 5.65. Alternately or in addition, the ZSM-5 may have a BET surface area in a range of from 115 to 135, 117.5 to 132.5, 120 to 130, 122.5 to 127.5, or 124 to 126 m$^2$/g. Alternately or in addition, the ZSM-5 may have a micropore volume in a range of from 0.04 to 0.06, 0.41 to 0.59, 0.42 to 0.58, 0.43 to 0.57, 0.44 to 0.55, 0.45 to 0.53, 0.46 to 0.52, 0.47 to 0.51, or 0.48 to 0.50 cm$^3$/g. Alternately or in addition, the ZSM-5 may have a mesopore volume in a range of from 0.03 to 0.05, 0.032 to 0.048, 0.034 to 0.046, 0.036 to 0.044, 0.038 to 0.042, or 0.039 to 0.041 cm$^3$/g, Alternately or in addition, the ZSM-5 may have a total acidity of 0.3 to 0.6, 0.33 to 0.575, 0.35 to 0.567, 0.367 to 0.55, 0.375 to 0.533, 0.4 to 0.525, 0.433 to 0.5125, or 0.466 to 0.5 mmol/g. The different zeolite may have a $SiO_2$-to-$Al_2O_3$ ratio in a range of from 2.5 to 4.5, 0.275 to 4.25, 0.3 to 0.4, 0.31 to 0.375, 0.32 to 0.35, or 0.325 to 0.333. Alternately or in addition, the different zeolite may have a BET surface area in a range of from 145 to 175, 147.5 to 170; 150 to 167.5, 152.5 to 165, 155 to 162.5, or 156 to 160 m$^2$/g. Alternately or in addition, the different zeolite may have a micropore volume in a range of from 0.05 to 0.07, 0.0525 to 0.06725, 0.055 to 0.0667, 0.0575 to 0.065, 0.060 to 0.064, or 0.061 to 0.063 cm$^3$/g. Alternately or in addition, the different zeolite may have a mesopore volume in a range of from 0.06 to 0.18, 0.08 to 0.16, 0.10 to 0.14, 0.11 to 0.13 cm$^3$/g. Alternately or in addition, the different zeolite may have a total acidity of 0.03 to 0.15, 0.04 to 0.14, 0.06 to 0.13, 0.07 to 0.12, 0.08 to 0.11, 0.0825 to 0.10, or 0.085 to 0.095 mmol/g. Of course, any of these endpoints may be exchanged with other ranges depending upon the desired effect.

The crude oil in the feed, particularly with light crude, preferably sweet, will generally be unfractionated. Useful crude oil(s) may have a sulfur content of no more than 10, 8, 7.5, 7, 6, 5, 4, 3, 2.5, 2, 1, 0.5, 0.1, 0.01, or 0.001 wt. f % of the total crude weight. Useful crude oil(s) may have an API gravity of at least 25, 26, 27, 28, 29, 30, 30.1, or 30.5°, though crudes of higher or lower API gravities, e.g., 10 to 25, 12.5 to 22.5, or 15 to 20, and/or more than 31, 35, 37.5, 40, or 45°, are likewise eligible for use. Additionally or separately, useful crude oil(s) may have no more than 20 17.5, 15, 10, 7.5, 5, 4, 3, 2, 1, or 0.5 ppm V, and/or 5, 4, 3.5, 3, 2.5, 2, 1.75, 1.5, 1.25, 1, 0.5, 0.1, 0.01, or 0.001 ppm Ni. Useful crudes may be, for example, Abu Bukhoosh (31.6°), Agbami (47.5°), Aktobe (41.6°), Al Shaheen (26.51°), Al-Jurf (30.0°). Alaska North Slope (31.9°) Alba (Eq. Guinea, 53.0°), Alba (U.K., 19.4°), Albian Heavy (19.6°), Algerian Condensate (68.7°), Amenam Blend (38.2°), Amenam/Mars Blend (33.5°), Ameriven-Hamaca (26°), Amna (36°), Anasuria, Antan Blend (26.4°), Arab Extra Light (39.4°), Arab Heavy (27.7°), Arab Light (32.8°), Arab Light/Seg 17 Blend (32.4°), Arab Medium (30.2°), Arab Super Light (50.1°), Arab Super Light Ardjuna (50.6), Arun Condensate, Aasgard Blend (50.5°), Attaka, Azadegan, Azeri BTC (36.1°), Azeri Light (34.8°), BCF-17 (16.5°), Bach Ho (33.8°), Bachaquero 17 (17°), Bachaquero 24 (24°), Balder (30.1°), Baobab (23°), Barrow (36.1°), Basrah Blend, Basrah Light (30.5°), Basrah Light/Mesa 30 Blend (30.5°), Bayou Choctaw Sour (32.2°), Bayou Choctaw Sweet (36.0°), Bayu Undan (55.9°), Belanak (47.8°), Belayim Blend (27.5°), Belida, Benchamas, Beryl (37.5°), Bintulu Condensate (69.3°), Usan (29.9°), Bonga (29.1°), Bonito Sour (35.5°), Bonny Light (33.4°), Bontang Condensate, Boscan (10.1°), Bouri (26.3°), Bow River (24.7°), Brass River, Brega (39.8°), Brent Blend (38.3°), Brunei Light, CPC Blend (45.3°), Cabinda (32.4°), Canadian Par (40°), Canadon Seco (25.7°), Cano Limon (30°), Captain (19.2°), Ceiba (29.9°), Cepu (32°), Cerro Negro (16°), Champion (28.7°), Chin Sao (40.1°), Chinguetti (28.3°), Cinta (31.1°), Clair (23.7°), Cold Lake (21.2°), Cooper (45.2°), Cossack (47.7°), Cusiana (44°), DUC (33.6°), Dalia (23.6°), Daqing (32.2°), Dar Blend (26.42°), Djeno (27.0°), Doba (21.1°), Doroud (34°), Draugen (39.9°), Dubai (31°), Dukhan (41.1°), Dulang (37.6°), Duni (20.8°), EA Crude (35.1°), East MS Mix (30.9°), Ekofisk Blend (Norway, 37.2°), Ekofisk Blend (U.K., 37.5°), El Sharara (43.1°), Enfield (21.7°), Erha (31.8°), Sidra (37°), Escalante (24.1°), Escravos (34.2°), ESPO blend (34.8°), Eugene Island (34.3°), Fateh (30.4°), Fife, Flotta (35.4°), Foinaven (26.6°), Forcalos (30.8°), Foroozan Blend (29.7°), Forties Blend (40.3°), Fulmar, Furrial (30.0°), Galeota Mix (37.8°), Gippsland (42°), Girassol (29.9°), Glitne (32.9°), Grane (18.7°), Gryphon, Gullfaks Blend (37.5°), Handil Mix (43.9°), Hanze, Harding (20.7°), Heavy Hardisty (22°), Heavy Louisiana Sweet (32.9°), Heidrun (25.0°), Hibernia (34.4°), Hungo Blend (29.1°), Iran Heavy (30.2°), Iran Light (33.1°), Isthmus (33.4°), Jasmine, Jotun, Karachaganak Condensate (44.7°), Kashagan (42-48°), Khafji (28.5°), Kikeh (34.9°), Kirkuk (33.9°), Kissanje Blend (29.8°), Kitina (36.4°), Kittiwake, Kole (32.1°), Kuito (19.0°), Kumkol (41.2°), Kutubu Blend (46.6°), Kuwait Blend (30.2°), Labuan (32.0°), Laguna (10.9°), Laminaria, LA Mississippi Sweet (40.7°), Lavan Blend (34.2°), Light Louisiana Sweet (35.6°), Lion Crude (39.6°), Liuhua, Liverpool Bay (45°), Lloyd Blend (20.9°), Lower Zakum (39.8°), Loreto (18.1°), Lufeng (33.3°), MacCulloch, Mandji (30°), Marib Light (Alif, 48.9°), Marlim (19.6°), Mars Blend (30.3°), Mars/Mesa Blend (40/60, 30.1°), Mars/Urals Blend (50/50, 31.1°), Masila (31.4°), Maureen (35.3°), Maya (21.8°), Mayna (21.5°), Medanito (34.9°), Mediterranean Sidi Kerir (Heavy, 30°), Mediterranean Sidi Kerir (Light, 34°), Mesa 30 (29.4°), Minas (35.3°), Miri (323°) Mixed Blend Sweet (41.0°), Mondo (28.8°), Turban (40.2°), Mutineer Exeter (43.4°), Naphtha Koch (57.8°), N'kossa (41.0°), NFC II (57.95°), Northwest Shelf Condensate (61.2°), Nang Nuang, Nanhai Light (40.1°), Napo (19°), Nemba (40.9°), New Zafiro Blend (29.5°), Nile Blend (33.9°), Njord (46.6°), Norne (30.8°), Nowruz/Soroush (18-19°), Odudu (30.5°), Oguendjo (27.3°), Okono (41.9°), Olmeca (37.3°), Oman Blend (34°), Oriente (24.1°), Ormen Lange condensate (52.3°), Oseberg Blend (37.8°), Oesgard Blend, Oso Condensate (45.7°), Palanca/Soyo Blend (37.8°), Panyu (28-32°), Peng Lai (21.8°), Pennington (35°), Peregrino (13.4°), Petrozuata Heavy (19.5°), Pierce, Plutonic (32.6°), Port Hudson (45.0°), Poseidon Streams (29.6°), Premium Albian (35.5°), Qatar Marine (35.8°), Qua Iboe (36.3°), Rabi Light (37.7°), Rang Doug (37.7°), Rincon (35.8°), Rio Grande do Norte (29.5°), Ross, Saharan Blend (45°), Santa Barbara (39.5°), Sarir (37.6°), Saudi Arabia Heavy (27°), Saudi Arabia Light (34°), Saudi Arabia Medium (31°), Saxi Batuque Blend (32.8°), Schiehallion Blend (25.5°), Senipah (51.9°), Seria Light (36.2°), Seria Light Export, Shah Deniz Condensate (47°), Shengli (24.2°), Siberian Light (35.1°), Sincor (30-32°), Siri (38.1°), Sirri (33.4°), Sirtica (42.2°), Sleipner Condensate (62.0°), Snorre, Snoehvit Condensate (60.1°), Sokol (Sakhalin I, 37.9°), Souedieh (24.1°), South Arne (37.71°), Southern Green Canyon (30.4°), South Louisiana Sweet (35.9°), Stag (18.5°), Stafjord (39.1°), Su Tu Den (Black Lion, 36°), Suez Blend, Syncrude Sweet Blend (30.5-33.6°), Syrian Light (37.7°), Tapis Blend (45.2°), Tempa Rossa, Tengiz (46.4°), Terra Nova (33.2°), Thamama Condensate (58.4°), Tia Juana Heavy (11°), Tia Juana Light (31.9°), Triton (37.5°), Troll Blend (35.8°), Turkmen Blend (33.0°), Ukpokiti (41.7°), Umm Shaif (36.5°), Upper Zakum (32.9°), Urals (to Mediterranean, 31.7°), Urucu (42.1°), Varg (37.9°), Vasconia (24.5°), Vityaz (Sakhalin II, 34.6°), Volve (27.9°), Wafra (24.5°), West Seno (38°), West Texas Intermediate (39.6°), West Texas Sour (31.7°), Western Canadian Select (20.3°), White Rose (29.8°), Widuri (33.2°), Williams Sugarland Blend (40.9°), Wytch Farm, Perenco, Xikomba (34.7°), Yoho Crude (39.3°), Zakum (40.2°), Zarzaitine (42.8°), Puerto Jose (32°), Zuwetina, or mixtures of these.

A feed for the FCC unit may comprise the mixture, i.e., comprising LCO and HCO, and vacuum gas oil (VGO) having a boiling range of from 250 to 585, 275 to 575, 300 to 560, 325 to 550, 350 to 525, 375 to 512.5, 400 to 500, 425 to 475, or 440 to 460° C. The FCC unit may directly downstream of the riser reactor, i.e., may have no intervening reactors, separators, regenerators, and/or isomerizers. The connection between the two crackers me be a direct feed line, or may proceed from a separator of the first cracker to the second cracker.

Inventive methods may comprise separating products from the FCC unit into fractions comprising light olefins, light cracked naphtha (LCN) having a boiling range of from 20 to below 121° C., heavy cracked naphtha (HCN) having a boiling range of from 121 to 221° C., light cycle oil (LCO) having a boiling range of from 221 to 343° C., and heavy cycle oil (HCO) having boiling points above 343° C. That is, the second cracker may separate at least at efficiently as the first cracker, preferably more, and may separate more fractions out of the feed than the first cracker. The second, i.e., FCC, cracker may allow for the production of a similar propylene yield or more than the first cracker. Light olefin feeds from the first and second cracker may be taken off in the same effluent.

The feeding may use a feed comprising the crude oil and 2 to 20, 3 to 18, 4, to 16, 5 to 15, 6 to 14, or 7.5 to 15 wt. % of the LCN, based on a total feed weight. The fluidized catalyst, i.e., E-Cat, may be different from the FCC catalyst, i.e., may have a different silica-to-alumina composition and/or may be of different atomic composition. A catalyst-to-oil weight ratio in the riser reactor and/or the FCC unit may be in a range of from 25 to 50, 30 to 45, 35 to 40, and/or at least 20, 22.5, 27.5, 32.5, 37.5, or 42.5, and/or no more than 60, 55, 47.5, 42.5, 17.5, or 32.5.

The catalyst particle diameter of may be other than 10 to 200 µm, i.e., at least 250, 275, 300, 325, 350, 375, 400, 425, 450, 475, or 500 µm. The FCC and/or first cracker catalyst may include (1) ZSM-5, ZSM-11 or beta zeolite, and (2) ZSM-5 or ZSM-11 zeolite, each on silica/alumina, though the catalyst will generally mix ZSM-5 with other zeolite(s).

The feed to the FCC unit and/or the LCN recycle, may limit C4 olefins to no more than 65, 50, 45, 40, 33, 25, 20, 15, 10, 7.5, 5, 4, 3, 2, 1, or 0.5 wt. %, relative to the total feed and/or recycle weight.

The LCN recycle may comprise no more than 15, 10, 7.5, 5, 4, 3, 2, 1, or 0.5 wt. %, relative to the total recycle weight, of overhead gas(es), such as methane, ethane, ethylene, propane, propylene, butane, butylene, and/or isobutene. The LCN recycle may comprise no more than 15, 10, 7.5, 5, 4, 3, 2, 1, or 0.5 wt. %, relative to the total recycle weight, of heavy and/or light cycle oil(s).

Aspects of the invention provide processes for producing light olefins (mainly ethylene and propylene) from catalytic cracking of whole light crude oil and integrating this cracking with an adjacent conventional FCC unit. This means that an original feedstream of a suitable crude oil, or substantially unfractionated crude component mixture, is fed to a cracker for cracking, then feeding at least a portion the cracked products, particularly liquid products, such as vacuum gas oil (VGO) to a second cracker (e.g., FCC), whereby light cracked naphtha may be cycled from the first cracker, second cracker, or both, back to either cracker. Light cracked naphtha (LCN) from the cracking of whole crude oil cracking and/or the FCC unit may be recycled for recracking with the fresh crude oil feed, and/or with the VGO feed. Heavy cracked naphtha (HCN) produced from crude oil cracking is sent to a gasoline pool while the light and heavy cycle oils are sent to the adjacent conventional FCC unit and mixed with fresh VGO feed.

The feed to the initial cracker (in the process described herein) may be light crude or shale oil with API gravity preferably higher than 30°, low sulfur (e.g., 5, 3, 2, or 1 wt % or less), and/or low heavy metal(s), e.g., Ni, V, etc., content. Whole crude oil may be cracked in an FCC apparatus including, for example, a catalyst hopper, short-contact time riser reactor, rapid disengagement (stripping), and/or continuous catalyst regeneration. Ethylene and propylene yields can depend on the composition of light crude oil, the FCC catalyst/ZSM-5 additive(s) used, and/or the operating, conditions of the cracking unit. An LCN product fraction from crude oil cracking and/or conventional FCC unit can be recycled and mixed with fresh crude oil or other hydrocarbon mixtures, prior to catalytic cracking in the riser reactor. The LCN fraction may have a final boiling point of about 121° C. (e.g., 110 to 132, 112 to 130, 114 to 128, 116 to 126, 118 to 124, or 120 to 122° C.) and contain C5 to C7 hydrocarbons including not mal paraffins, iso-paraffins, olefins, naphthenes, and mono-aromatics.

The LCN can be mixed with fresh light crude oil at 1 to 40, 2 to 20, 3 to 18, 4 to 16, or 5 to 15 wt %, based on a total feed weight. The crude oil and LCN mixture may have a residence time in the riser of less than 2.5, 2.0, 1.5, 1.0, 0.75, 0.5, or 0.25 seconds. The catalyst-to-oil ratio may be 20 to 60, 25 to 50, 30 to 45, 33 to 40, or 35 to 37.5 (wt/wt). The riser reactor can be operated at pressure in the range of from 0.1 to 10, 0.25 to 5.0, 0.5 to 2.0, 0.75 to 1.5, 0.9 to 1.1 bar and/or a temperature in the range of from 500 to 1000, 550 to 800, 600 to 700, 625 to 675, 633 to 667, or 645 to 660° C. Based on micro-activity testing results, the cracking of light crude oil and LCN mixture may result in slightly increasing the yields of ethylene and propylene at levels similar to the cracking of light whole crude oil alone.

After the reaction, spent or coked catalyst can be separated from cracked hydrocarbon product in the upper part of the riser reactor using cyclones. Then the spent catalyst can be stripped from remaining hydrocarbons, for example, using steam in the stripper at suitable temperature. The spent catalyst may then be sent to a regenerator. e.g., for combusting deposited coke in an oxidizing atmosphere at temperatures above 650, 700, 750, or 800° C.

Inventive catalyst(s) for catalytic cracking of whole light crude oil may be a mixture of USY zeolite FCC catalyst blended with high-ZSM-5 content additive. ZSM-5 additive (s) may be physically blended with FCC catalyst(s) at 2.5 to 50, 5 to 40, 10 to 38, 20 to 36, 20 to 35, or 25 to 30 wt %. The FCC catalyst(s) and ZSM-5 additive(s) may be available commercially, e.g., from FCC catalyst manufacturers.

The flow diagram in FIG. 1 shows that that a crude oil cracking unit 100 can be integrated with the conventional fluid catalytic cracking (FCC) unit 200 utilizing a product light cycle oil (LCO) and heavy cycle oil (HCO) stream 106 as a co-feed with vacuum gas oil (VCO) 201 for fluid catalytic cracking (FCC) unit. The light naphtha product from vacuum gas oil (VGO) cracking, light cracked naphtha (LCN) 204, can be mixed with light cracked naphtha (LCN) 104 from crude oil cracking Both streams are recycled for mixing with fresh crude oil feed 102.

EXAMPLES

The pre sent invention is further illustrated in the following non-limiting examples, in which the catalytic cracking of various crude oils and light cracked naphtha (LCN) was conducted in a fixed-bed microactivity test (MAT) unit according to ASTM D-3907. The tests were conducted at a temperature of 650° C., catalyst-to-oil (C/O) ratio of 6.0 g/g, and time-on-stream (TOS) of 30 seconds. Dry gas ($H_2$ and $C_1$ to $C_2$) and liquefied or liquid petroleum gas (LPG, $C_3$ to $C_4$) were analyzed using a gas chromatography (GC) with four thermal conductivity detectors. Three liquid product fractions were defined as: naphtha (light and heavy at $C_5$ to 221° C.), light cycle oil-LCO (221 to 343° C.) and heavy cycle oil-HCO (at least 343° C.). The conversion was defined as the total amount of product gas and coke. The physical and distillation properties of the various light crude oils used in the microactivity test (MAT) experiments are presented below in Table 1.

TABLE 1

Physical and distillation properties of various light crude oils used as feeds in microactivity test (MAT) testing

| Property | Arabian Light (AL) | Arabian Extra Light (AXL) | Arabian Super Light (ASL) |
|---|---|---|---|
| Gravity, ° API | 34 | 39.3 | 51.3 |
| Density at 15° C., kg/m³ | 892 | 828 | 774 |
| Sulfur (wt. %) | 2.3 | 1.6 | 0.11 |
| Vanadium (ppm) | 16 | 2.7 | 1 |
| Nickel (ppm) | 3.3 | <1 | <1 |
| Microcarbon residue (wt. %) | 3.6 | 2.20 | 0.46 |
| Kin. Viscosity, @ 21° C. (cSt) | 10.2 | 5.8 | 2.3 |
| Elemental analysis (wt. %) | | | |
| Carbon | 84.3 | 84.3 | 85,3 |
| Hydrogen | 12.2 | 12.6 | 14.0 |
| Nitrogen | 0.64 | 0.70 | 0.53 |
| Simulated distillation (° C.) | | | |
| Initial boiling point | 22 | 25 | 22 |
| 50% | 307 | 287 | 242 |
| Final boiling point | 580 | 577 | 558 |
| Distillation cuts (wt. %) | | | |
| Light naphtha ($C_5$-121° C.) | 12 | 13 | 19 |
| Heavy naphtha (121-221° C.) | 23 | 25 | 31 |
| Middle distillates (221-343° C.) | 26 | 27 | 29 |
| Heavy oil (343° C.+) | 39 | 35 | 21 |
| PIONA naphtha fraction (wt. %) | 46/18/0/9/27 | 34/31/0/8/27 | 34/32/0/19/15 |
| UOP K-Factor | 11.76 | 12.0 | 12.55 |

The commercial equilibrium catalyst ("E Cat" which is generally a different zeolite) used in the microactivity test (MAT) experiments was calcined at 500° C. for 3 hours at a rate of 5° C./minute before use. The commercial fresh ZSM-5 was treated in 100% steam at 810° C. for 6.0 hours. The chemical and physical properties of the E-Cat (different zeolite) and ZSM-5 are presented in Table 2, below.

TABLE 2

Physico-chemical properties of E-Cat and ZSM-5 additive

| Property | E-Cat | ZSM-5 Additive |
|---|---|---|
| $SiO_2/Al_2O_3$ ratio[a] | 3.30 | 5.61 |
| BET surface area, $m^2/g$[b] | 157 | 126 |
| Micropore volume, cc/g | 0.062 | 0.049 |
| Mesopore volume, cc/g | 0.12 | 0.04 |
| Total acidity ($NH_3$•TPD), mmol/g[c] | 0.09 | 0.49 |

[a]Measured by ICP analysis;
[b]Determined by t-plot;
[c]Calculated using high-temperature $NH_3$ desorption peak In all the microactivity test (MAT) experiments described herein, the E-Cat/ZSM-5 mixture was prepared by physical mixing of 70 wt. % E-Cat and 30 wt. % ZSM-5. The simulated distillation results of the light cracked naphtha (LCN) and its mixture with various crude oils are presented in Table 3, below.

TABLE 3

Simulated distillation of light cracked naphtha (LCN) and of mixtures of crude oil with naphtha

| Temp. Range, °C. (Fraction) | LCN | 85% AL + 15% LCN | 75% AL + 25% LCN | 85% AXL + 15% LCN | 85% ASL + 15% LCN |
|---|---|---|---|---|---|
| 20-121 (Light Naphtha) | 98 | 20 | 31 | 19 | 24 |
| 121-221 (Heavy Naphtha) | 2 | 21 | 19 | 23 | 29 |
| 221-343 (Middle Distillates) | 0 | 24 | 20 | 25 | 28 |
| 343+ (Heavy Oil) | 0 | 35 | 30 | 11 | 19 |

Recovery, wt %

The n-paraffins, i-paraffins, olefins, naphthenes, and aromatics (PIONA) composition of the LCN is presented in Table 4, below.

TABLE 4

PIONA analysis of light cracked naphtha (LCN)

| Fraction, wt% | C5 | C6 | C7 | Total |
|---|---|---|---|---|
| n-Paraffins | 3.8 | 1.8 | 0.8 | 6.4 |
| i-Paraffins | 22.3 | 12.9 | 4.2 | 39.4 |
| Olefins | 20.1 | 2.9 | 3.3 | 26.3 |
| Naphthenes | — | 3.9 | 3.2 | 7.1 |
| Aromatics | — | 12.6 | 7.7 | 20.3 |
| Total | 46.2 | 34.1 | 19.2 | 99.5 |

Example 1

This example illustrates the catalytic and thermal cracking of Arabian Light (AL) crude oil and light cracked naphtha (LCN) at 650° C. The catalytic conversion of Arabian Light was about 60 wt. % compared with 33 wt. % for thermal cracking. The yields of ethylene and propylene from Arabian Light catalytic cracking were 10.7 wt % and 19.2 wt. %, respectively, compared with 7.6 wt. % and 8.6 wt % for thermal cracking. Similar performance was found in the cracking of light cracked naphtha (LCN) with catalytic conversion reaching 53 wt. % compared with 29.3 wt. % for them al cracking. In light cracked naphtha (LCN) catalytic cracking, the yields of ethylene and propylene were 11.6 wt. % and 19.3 wt. %, respectively. The yield of light and heavy cycle oil (LCO, HCO) was 17.1 wt. % in Arabian Light catalytic cracking and 32.0 wt. % in thermal cracking compared with 65 wt % in the fresh Arabian Light feed. The microactivity test (MAT) product yields are presented in Table 5.

The results of this example clearly show the advantages of catalytic cracking for the production of light olefins and the cracking of light and heavy cycle oil (LCO, HCO) feed fraction compared with thermal cracking case.

TABLE 5

Product yields from the catalytic and thermal cracking of Arabian Light (AL) crude oil and light cracked naphtha (LCN) at 650° C.

| Item | Arabian Light Crude Oil (AL) | | Light Cracked Naphtha (LCN) | |
|---|---|---|---|---|
| | E-Cat/ZSM-5 | Thermal | E-Cat/ZSM-5 | Thermal |
| Catalyst/oil ratio, g/g | 6.07 | — | 6.99 | — |
| Conversion, wt % (gas + coke) | 59.86 | 33.58 | 53.11 | 29.25 |
| Mass balance, % | 92.3 | 89.9 | 90.2 | 86.3 |
| Product yield, wt % | | | | |
| Dry gas | 21.01 | 15.75 | 20.03 | 10.00 |
| $H_2$ | 0.34 | 0.15 | 0.20 | 0.08 |
| $C_1$ | 5.65 | 4.58 | 4.53 | 3.89 |
| $C_2$ | 4.11 | 3.44 | 3.66 | 2.03 |
| $C_2^=$ | 10.69 | 7.587 | 11.64 | 4.00 |
| LPG | 33.51 | 17.05 | 32.29 | 19.25 |
| $C_3$ | 2.87 | 0.93 | 3.32 | 0.21 |
| $C_3^=$ | 19.23 | 8.57 | 19.27 | 6.40 |
| $C_4^=$ | 9.21 | 6.69 | 8.21 | 12.60 |
| $n-C_4$ | 0.94 | 0.152 | 0.88 | 0.02 |
| $i-C_4$ | 1.26 | 0.71 | 0.61 | 0.03 |
| $C_2^=$ to $C_4^=$ | 39.13 | 22.85 | 39.12 | 23.00 |
| Naphtha | 23.05 | 34.40 | 43.85 | 70.23 |
| LCN | 4.82 | 9.96 | 23.91 | 64.38 |
| HCN | 18.23 | 24.43 | 19.94 | 5.85 |
| LCO | 10.86 | 17.33 | 2.69 | 0.15 |
| HCO | 6.24 | 14.70 | 0.34 | 0.36 |
| Coke | 5.34 | 0.78 | 0.78 | 0.00 |

Example 2

In Example 2, the recycling of light cracked naphtha (LCN) was simulated by mixing Arabian Light (AL) crude oil feed and light cracked naphtha (LCN) in varying proportions (15 and 25% LCN). The mixing of Arabian Light crude oil with 15 wt. % versus 25 wt. % light cracked naphtha (LCN) showed slight increase in propylene yield from 19.2 wt. % in Arabian Light crude oil alone compared with 19.8 wt. % in Arabian Light crude oil mixing with 15 wt. % versus 25 wt. % light cracked naphtha (LCN). Ethylene yield decreased slightly from 10.7 wt. % in Arabian Light crude oil alone, compared with to 10.1 wt. % in Arabian Light crude oil mixed with 15 wt. % light cracked naphtha (LCN), or 10.5 wt % in Arabian Light crude oil mixing with 25 wt. % light cracked naphtha (LCN). The main change was seen in the yield of coke which dropped from 5.3 wt. % to 3.5 wt. % in Arabian Light crude oil mixing with 15 wt. % light cracked naphtha (LCN). The results indicate that the recycling of light cracked naphtha (LCN) to fresh crude oil feed maintains or slightly increase the yields of C2 to C4 light olefins. The conversion and product yields are presented in Table 6.

TABLE 6

Product yields from catalytic cracking of Arabian Light (AL) crude oil and mixtures of AL with light cracked naphtha (LCN) over E-Cat/ZSM-5 at 650° C.

| | MAT Feed | | |
|---|---|---|---|
| Item | AL Crude oil | 0.85 AL + 0.15 LCN | 0.75 AL + 0.25 LCN |
| Catalyst/oil ratio, g/g | 6.07 | 5.67 | 5.96 |
| Conversion, wt % (gas + coke) | 59.86 | 56.83 | 56.80 |
| Mass balance, % | 92.3 | 91.6 | 94.51 |
| Product yield, wt % | | | |
| Dry gas | 21.01 | 18.26 | 19.34 |
| $H_2$ | 0.34 | 0.27 | 0.27 |
| $C_1$ | 5.65 | 4.43 | 4.88 |
| $C_2$ | 4.32 | 3.51 | 3.67 |
| $C_2^=$ | 10.69 | 10.05 | 10.52 |
| LPG | 33.51 | 35.08 | 34.24 |
| $C_3$ | 2.87 | 3.25 | 3.15 |
| $C_3^=$ | 19.23 | 19.76 | 19.76 |
| $C_4^=$ | 9.21 | 9.56 | 9.20 |
| n-$C_4$ | 0.94 | 1.16 | 1.00 |
| i-$C_4$ | 1.26 | 1.34 | 1.13 |
| $C_2^=$ to $C_4^=$ | 39.13 | 39.38 | 39.48 |
| Naphtha | 23.05 | 26_60 | 28.06 |
| LCN | 4.82 | 6.48 | 8.21 |
| HCN | 18.23 | 20.13 | 19.85 |
| LCO | 10.86 | 10.40 | 9.40 |
| HCO | 6.24 | 6.17 | 5.75 |
| Coke | 5.34 | 3.49 | 3.21 |

Example 3

Figure 2:
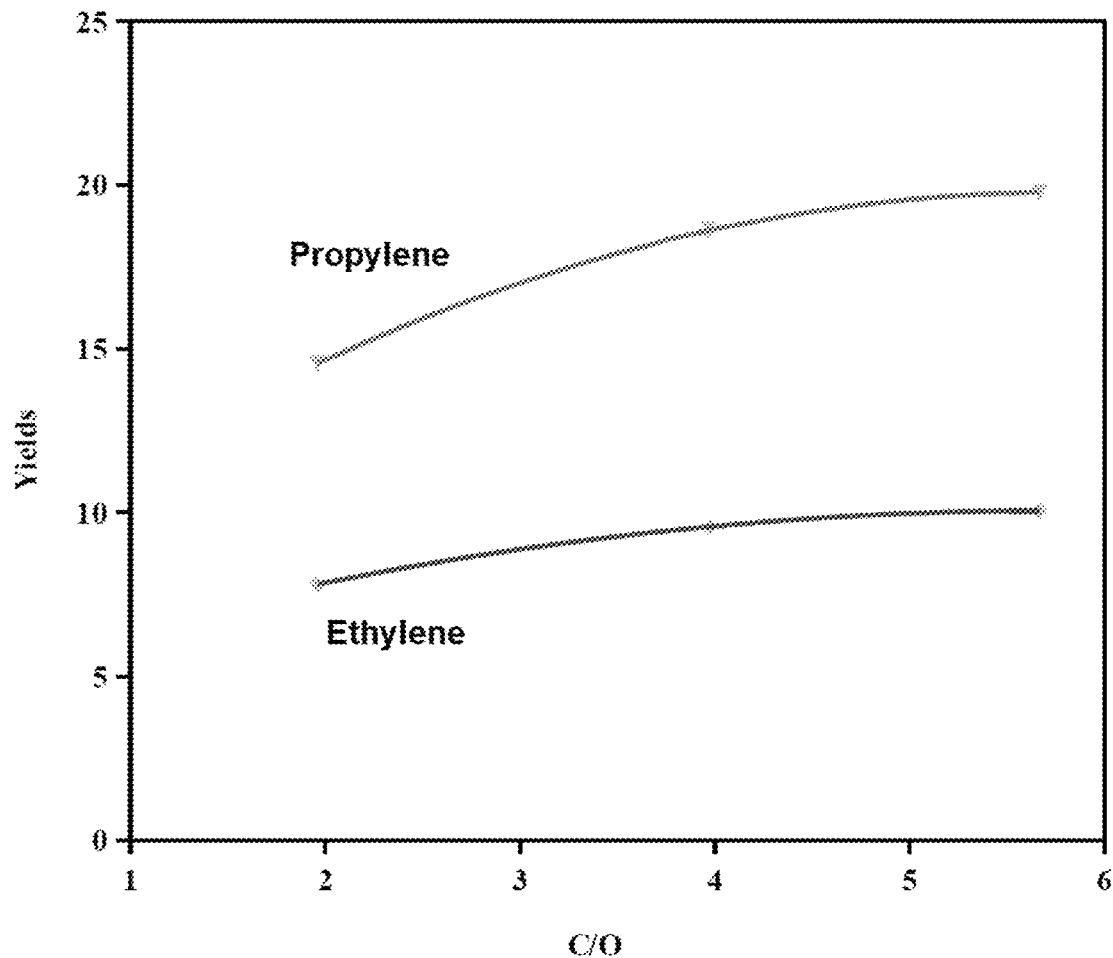
FIG. 2 shows the effect of catalyst-to-oil ratio on the yield of ethylene and propylene from the catalytic cracking of 85 wt. % Arabian Light crude oil and 15 wt. % light cracked naphtha at 650° C.

Example 3 presents the effect of catalyst/oil (C/O) ratio on the yields of ethylene and propylene from the cracking 85 wt. % of Arabian Light (AL) crude oil with 15 wt. % at 650° C. The results are shown in FIG. 2, Ethylene yield increased by 27% reaching 10 wt % and propylene yield increased by 34% reaching 19.8 wt % at C/O ratio of 5.7. Similarly, microactivity test (MAT) conversion increased with increasing C/O ratio, reaching 53 wt. % at a C/O ratio of 5.7. The increase in the yield of light olefins was associated with a decrease in the yield of liquid fractions, mainly naphtha yield. The results of Example 3 show that high yields of light olefins are favored in cracking a mixture comprising Arabian Light (AL) crude oil and light cracked naphtha (LCN) using E-Cat/ZSM-5 at high C/O ratio.

Example 4

The results of the catalytic cracking of two light crude oils with API gravities above 30, namely Arabian Extra. Light (AXL) with an API gravity of 39° and Arabian Super Light (ASL) with an API gravity of 51° and their mixtures with LCN at 650° C. are presented in Table 7, below. The properties of these crude oils are presented in Table 1, above. The conversion of Arabian Extra Light (AXL) crude oil was about 59 wt. %, and the conversion of Arabian Super Light (ASL) crude oil was about 61 wt. %. Similarly to the microactivity test (MAT) results for the catalytic cracking of Arabian Light (AL) crude oil in Example 1, the yields of ethylene and propylene for Arabian Extra Light (AXL) crude oil ere 10.9 wt % (ethylene) and 20.3 wt % (propylene), respectively, compared with 10.6 wt. % and 21.6 wt. % for Arabian Super Light (ASL) crude oil. The yield of the light and heavy cycle oil (LCO, HCO) product fraction was 117 wt. % for Arabian Extra Light (AXL) and 7.6 wt. % for Arabian Super Light (ASL) crude oil. The mixing of light cracked naphtha (LCN) with both crude oils slightly impacted the yields of light olefins. The results of Example 4 show that the cracking of light crude oils using E-Cat/ZSM-5 at 650° C. produces a high yield of ethylene and propylene (above 30 wt. %) and low yield of light and heavy cycle oils (less than 15 wt. %).

TABLE 7

Product yields from the catalytic cracking of Arabian Extra Light (AXL) and Arabian Super Light (ASL) crude oils at 650° C.

| Item | AXL crude oil | 0.85 AXL + 0.15 LCN | ASL Crude oil | 0.85AXL + 0.15 LCN |
|---|---|---|---|---|
| Catalyst/oil ratio, g/g | 5.54 | 6.09 | 6.12 | 6.87 |
| Conversion, wt % (gas + coke) | 58.93 | 57.72 | 60.76 | 61.48 |
| Mass balance, % | 92.73 | 99.12 | 96.13 | 97.12 |
| Product yield, wt % | | | | |
| Dry gas | 19.84 | 19.53 | 18.58 | 19.82 |
| $H_2$ | 0.32 | 0.28 | 0.32 | 0.321 |
| $C_1$ | 4.78 | 4.74 | 4.42 | 4.72 |
| $C_2$ | 183 | 3.65 | 3.25 | 3.42 |
| $C_2^=$ | 10.91 | 10.87 | 10.58 | 11.37 |
| LPG | 35.95 | 35.43 | 40.76 | 40.23 |
| $C_3$ | 3.43 | 3.48 | 3.82 | 3.930 |
| $C_3^=$ | 20.30 | 20.26 | 21.61 | 21.84 |
| $C_4^=$ | 9.78 | 9.43 | 10.73 | 10.40 |
| n-$C_4$ | 1.25 | 1.20 | 2.28 | 2.06 |
| i-$C_4$ | 1.18 | 1.06 | 2.31 | 1.2 |
| $C_2^=$ to $C_4^=$ | 40.99 | 40.55 | 42.92 | 43.61 |
| Naphtha | 27.40 | 30.04 | 31.68 | 33.00 |
| LCN | 6.57 | 8.03 | 9.42 | 11.17 |
| HCN | 20.83 | 22.00 | 22.26 | 21.83 |
| LCO | 9.86 | 8.72 | 6.27 | 4.70 |
| HCO | 3.82 | 3.53 | 1.30 | 0.82 |
| Coke | 3.14 | 2.76 | 1.42 | 1.42 |

Referring now to the drawings, wherein like reference numerals designate identical or corresponding parts throughout the several views.

In the flow diagram shown in FIG. 1, a whole crude oil stream 101 is mixed with a recycled light cracked naphtha (LCN) product stream 107, to give combined feed stream 102, and fed to a preheater (not shown) prior to entering the riser reactor of the catalytic cracker 100. The catalytic cracker in FIG. 1 comprises a riser reactor, reaction section, a stripper, and catalyst regeneration, though replicated, additional, and/or alternate units may be employed. The feed mixture in FIG. 1 is contacted with hot catalyst coming from the regenerator (not shown) and the cracking is conducted at exemplary temperature(s) in a range of from 625 to 675° C. After the reaction, the catalyst is stripped from hydrocarbons using steam and sent for product fractionation. Gases, including dry gas and liquefied petroleum gas (LPG), are sent for product separation 110 for separating ethylene 111, propylene 112 and other gases 113. The liquid products are separated into the following cuts: light cracked naphtha (LCN) 104 for recycle with fresh feed; heavy cracked naphtha (HCN) 105 for gasoline pool; and light cycle oil (LCO) with heavy cycle oil (HCO) 106 for mixing with vacuum gas oil (VGO) feed 201 stream. The feed mixture 202 stream (VGO, LCO, and HCO) is fed into a conventional fluid catalytic cracking (FCC) unit 200 for cracking at typical FCC operating conditions. The cracked products are separated into gas stream 203 and other liquids products comprising light cracked naphtha (LCN) 204 for mixing with light cracked naphtha (LCN) 104, heavy cracked naphtha (HCN) 205, light cycle oil (LCO) 206, and heavy cycle oil (HCO) 207.

The flow diagram in FIG. 1 shows that crude oil cracking unit 100 is integrated with the conventional FCC unit 200 by using the product LCO and HCO stream 106 as a co-feed with VGO 201 for FCC unit 200. Moreover, the light naphtha product 204 from VGO cracking, i.e., LCN 204, is mixed with LCN 104 from crude oil cracking. Both streams are recycled for mixing with fresh crude oil feed 102.

FIG. 2 shows the results of Example 3, which studies the effect of catalyst/oil (C/O) ratio on the yields of ethylene and propylene from the cracking 85 wt. % of Arabian Light (AL) crude oil with 15 wt. % at 650° C. Ethylene yield increased by 27% reaching 10 wt. % and propylene yield increased by 34% reaching 19.8 wt. % at C/O ratio of 5.7. Similarly, microactivity test (MAT) conversion increased with increasing C/O ratio reaching 53 wt. % at C/O=5.7. The increase in the yield of light olefins was associated with a decrease in the yield of liquid fractions, mainly naphtha yield. The results of this example show that high yields of light olefins from the cracking of of Arabian Light (AL) crude oil and light cracked naphtha (LCN) mixture using E-Cat/ZSM-5 are favored at high GO ratio.

Numerous modifications and variations of the present invention are possible in light of the above teachings. It is therefore to be understood that within the scope of the appended claims, the invention may be practiced otherwise than as specifically described herein.

REFERENCE SIGNS 100 catalytic cracker
101 feed stream, e.g., whole or incompletely fractionated crude oil
102 feed plus light cracked naphtha (LCN) recycle
103 light gases
104 light cracked naphtha (LCN)
105 heavy cracked naphtha (HCN)
106 light cycle oil (LCO) with heavy cycle oil (HCO)
107 light cracked naphtha (LCN) recycle
110 product separator
111 ethylene
112 propylene
113 other gases
200 conventional or other FCC unit
201 vacuum gas oil (VGO) feed stream
202 vacuum gas oil (VGO) with light and heavy cycle oil (LCO, HCO)
203 gas stream
204 light cracked naphtha (LCN)
205 heavy cracked naphtha (HCN)
206 light cycle oil (LCO)
207 heavy cycle oil (HCO)

The invention claimed is:

1. A method, comprising:
feeding a crude oil to a riser reactor comprising a fluidized catalyst for cracking at a temperature in a range of from 625 to 800° C., the crude oil being at least 75 wt. % unfractionated, to obtain cracked products;
separating the cracked products into a first set of fractions comprising light olefins, light cracked naphtha (LCN) having a boiling range of from 20 to less than 121° C., heavy cracked naphtha (HCN) having a boiling range of from 121 to less than 221° C., and separate or combined fractions of light cycle oil (LCO) and heavy cycle oil (HCO),
wherein a separate fraction of LCO, if present, has a boiling range of from 221 to 343° C., and
wherein a separate fraction of HCO, if present, has a boiling point of above 343° C.;
co-feeding vacuum gas oil and a mixture consisting of at least portions of the LCO and the HCO from the separate or combined fractions of LCO and HCO to a fluid catalytic cracker (FCC) unit comprising an FCC catalyst, to obtain additional cracked products,
wherein the vacuum gas oil has a boiling range of from 250 to 585° C., and
wherein the FCC unit is fed only vacuum gas oil, LCO, and HCO,
separating the additional cracked products into a second set of fractions comprising LCN;
cycling at least a portion of the LCN from the first set of fractions and at least a portion of the LCN from the second set of fractions back to the feeding with the crude oil; and
optionally repeating the feeding, the separating of the cracked products, the co-feeding, the separating of the additional cracked products, and the cycling.

2. The method of claim 1, wherein the light olefins comprise at least 25 wt. % ethylene and propylene, based on the total weight of the light olefins.

3. The method of claim 1, wherein the riser reactor is operated at a pressure in a range of from 0.5 to 2.0 bar.

4. The method of claim 1, wherein the riser reactor is operated at a temperature in a range of from 630 to 700° C.

5. The method of claim 1, wherein the FCC catalyst comprises:
ZSM-5 in an amount in a range of from 10 to 40 wt. % of the total FCC catalyst weight; and
a different zeolite in an amount of at least 50 wt. % of the total FCC catalyst weight,
wherein the different zeolite has a $SiO_2$-to-$Al_2O_3$ ratio in a range of from 2.5 to 4.5, a BET surface area in a range of from 145 to 175 $m^2/g$, a micropore volume in a range of from 0.05 to 0.07 $cm^3/g$, a mesopore volume in a range of from 0.06 to 0.18 $cm^3/g$, and/or a total acidity of 0.03 to 0.15 mmol/g.

6. The method of claim 1, wherein the crude oil is unfractionated.

7. The method of claim 1, wherein the crude oil has an API gravity of at least 30°.

8. The method of claim 1, wherein crude oil comprises no more than 5 wt. % sulfur, 20 ppm V, and/or 5 ppm Ni.

9. The method of claim 1, wherein the separate or combined fractions of LCO and HCO are not subject to any intervening reaction, catalyst regeneration, or separation zone after exiting the riser reactor and before entering the FCC unit.

10. The method of claim 1, wherein the second set of fractions further comprises light olefins, heavy cracked naphtha (HCN) having a boiling range of from 121 to less than 221° C., light cycle oil (LCO) having a boiling range of from 221 to 343° C., and heavy cycle oil (HCO) having boiling points above 343° C.

11. The method of claim 1, wherein the feeding uses a feed comprising the crude oil and 2 to 20 wt. % of the LCN, based on the total weight of the feed.

12. The method of claim 1, wherein the separating does not produce separate fractions of LCO and HCO.

13. The method of claim 5, wherein the ZSM-5 has a $SiO_2$-to-$Al_2O_3$ ratio in a range of from 4.5 to 6.5, a BET surface area in a range of from 115 to 135 $m^2/g$, a micropore volume in a range of from 0.04 to 0.06 $cm^3/g$, a mesopore volume in a range of from 0.03 to 0.05 $cm^3/g$, and/or a total acidity of 0.3 to 0.6 mmol/g.

14. The method of claim 1, wherein the fluidized catalyst is different from the FCC catalyst.

15. The method of claim 1, wherein a catalyst-to-oil weight ratio in the riser reactor and/or the FCC unit is in a range of from 25 to 50.

16. The method of claim 1, wherein the FCC catalyst comprises:
- ZSM-5 in an amount in a range of from 10 to 40 wt. % of total FCC catalyst weight; and
- a different zeolite in an amount of at least 50 wt. % of the total FCC catalyst weight,
- wherein the different zeolite is ZSM-11, beta zeolite, or USY zeolite.

17. The method of claim 1, wherein at least a portion of the LCN from the first set of fractions and at least a portion of the LCN from the second set of fractions has a boiling point in a range of 118 to less than 121° C.

18. The method of claim 1, wherein the riser reactor is fed only the crude oil and LCN.

19. The method of claim 18, wherein the LCN has a boiling point in a range of 118 to less than 121° C.

20. The method of claim 1, wherein the HCN has a boiling point in range of 125 to 215° C.

* * * * *